(12) United States Patent
Daiss et al.

(10) Patent No.: US 8,168,818 B2
(45) Date of Patent: May 1, 2012

(54) METHOD FOR PRODUCING ISOCYANATES

(75) Inventors: Andreas Daiss, Deidesheim (DE);
Andreas Woelfert, Bad Rappenau (DE);
Carsten Knoesche, Niederkirchen (DE);
Eckhard Stroefer, Mannheim (DE)

(73) Assignee: BASF Aktiengesellschaft,
Ludwigshafen (DE)

( * ) Notice: Subject to any disclaimer, the term of this patent is extended or adjusted under 35 U.S.C. 154(b) by 0 days.

(21) Appl. No.: 12/447,940

(22) PCT Filed: Nov. 6, 2007

(86) PCT No.: PCT/EP2007/061932
§ 371 (c)(1),
(2), (4) Date: Apr. 30, 2009

(87) PCT Pub. No.: WO2008/055899
PCT Pub. Date: May 15, 2008

(65) Prior Publication Data
US 2010/0076218 A1    Mar. 25, 2010

(30) Foreign Application Priority Data

Nov. 7, 2006 (EP) .................................. 06123629

(51) Int. Cl.
*C07C 263/00* (2006.01)
(52) U.S. Cl. ...................................................... 560/347
(58) Field of Classification Search ........................ None
See application file for complete search history.

(56) References Cited

U.S. PATENT DOCUMENTS

| | | | |
|---|---|---|---|
| 4,847,408 A | 7/1989 | Frosch et al. | |
| 5,391,683 A | 2/1995 | Joulak et al. | |
| 5,449,818 A | 9/1995 | Biskup et al. | |
| 5,633,396 A | 5/1997 | Bischof et al. | |
| 5,679,839 A | 10/1997 | Armand et al. | |
| 6,225,497 B1 | 5/2001 | Becker et al. | |
| 7,488,842 B2 * | 2/2009 | Knoesche | 560/347 |
| 2004/0068137 A1 | 4/2004 | Herold et al. | |
| 2008/0027242 A1 | 1/2008 | Knosche et al. | |

FOREIGN PATENT DOCUMENTS

| | | |
|---|---|---|
| EP | 0 289 840 | 11/1988 |
| EP | 0 570 799 | 11/1993 |
| EP | 0 593 334 | 4/1994 |
| EP | 0 699 657 | 3/1996 |
| EP | 0 749 958 | 12/1996 |
| EP | 0 928 785 | 7/1999 |
| EP | 1 403 248 | 3/2004 |
| WO | 2005 123665 | 12/2005 |

OTHER PUBLICATIONS

U.S. Appl. No. 12/678,771, filed Mar. 18, 2010, Knoesche, et al.
U.S. Appl. No. 13/001,681, filed Dec. 28, 2010, Knoesche, et al.

* cited by examiner

*Primary Examiner* — Daniel Sullivan
*Assistant Examiner* — Jennifer C Sawyer
(74) *Attorney, Agent, or Firm* — Oblon, Spivak, McClelland, Maier & Neustadt, L.L.P.

(57) ABSTRACT

The invention relates to a process for preparing isocyanates in the gas phase.

17 Claims, 4 Drawing Sheets

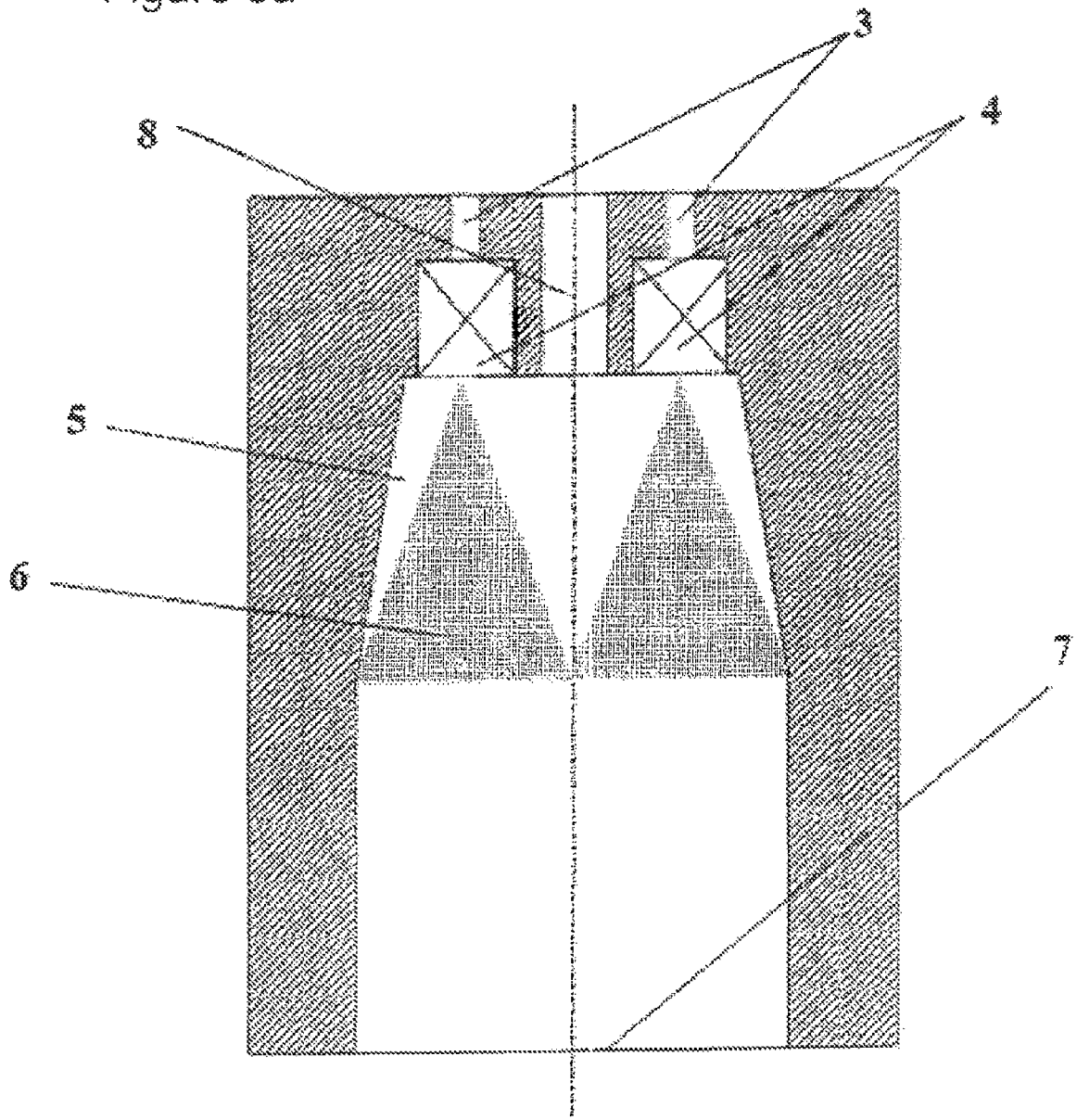

METHOD FOR PRODUCING ISOCYANATES

The present invention relates to a process for preparing isocyanates in the gas phase.

Isocyanates are produced in large quantities and serve mainly as starting materials for producing polyurethanes. They are usually prepared by reacting the corresponding amines with phosgene.

One possible way of preparing isocyanates is reaction in the gas phase. The advantages of this mode of operation are a reduced phosgene holdup, avoidance of intermediates which are difficult to phosgenate and increased reaction yields. Apart from effective mixing of the feedstreams, achievement of a narrow residence time spectrum and adherence to a narrow residence time window are important prerequisites for such a process to be able to be carried out industrially. These requirements can be met, for example, by the use of tube reactors operated with turbulent flow or by means of flow tubes having internals.

Various processes for preparing isocyanates by reacting amines with phosgene in the gas phase are known from the prior art.

EP-A-593 334 describes a process for preparing aromatic diisocyanates in the gas phase, wherein the reaction of the diamine with phosgene takes place in a tube reactor which has no moving parts and has a constriction of the walls along the longitudinal axis of the tube reactor. However, the process is problematical since mixing of the feedstreams purely by means of a constriction of the tube wall functions poorly compared to use of a correct mixing device. Such poor mixing usually leads to undesirably high solids formation.

EP-A-699 657 describes a process for preparing aromatic diisocyanates in the gas phase, wherein the reaction of the associated diamine with the phosgene takes place in a two-zone reactor in which the first zone, which makes up from 20% to 80% of the total reactor volume, is ideally mixed and the second zone, which makes up from 80% to 20% of the total reactor volume, can be characterized by plug flow. However, because at least 20% of the reaction volume is ideally backmixed, there is a nonuniform residence time distribution which can lead to undesirably increased solids formation.

EP-A-289 840 describes the preparation of diisocyanates by gas-phase phosgenation, in which the preparation takes place, according to the invention, in a turbulent stream at temperatures of from 200° C. to 600° C. in a cylindrical space without moving parts.

The omission of moving parts reduces the risk of phosgene escaping. The turbulent flow in the cylindrical space (tube) results, if fluid elements in the vicinity of the wall are disregarded, in a good equalized flow in the tube and thus a narrow residence time distribution which can, as described in EP-A-570 799, lead to a reduction in solids formation.

EP-A-570 799 relates to a process for preparing aromatic diisocyanates in the gas phase, wherein the reaction of the associated diamine with the phosgene is carried out in a tube reactor above the boiling point of the diamine within a mean contact time of from 0.5 to 5 seconds. As described in the document, both reaction times which are too long and reaction times which are too short lead to undesirable solids formation. A process in which the mean deviation of the mean contact time is less than 6% is therefore disclosed. Adherence to this contact time is achieved by carrying out the reaction in a stream in the tube which is characterized either by a Reynolds number of greater than 4000 or a Bodenstein number of greater than 100.

EP-A-749 958 describes a process for preparing triisocyanates by gas-phase phosgenation of (cyclo)aliphatic triamines having three primary amino groups, wherein the triamine and the phosgene are continuously reacted with one another at a flow velocity of at least 3 m/s in a cylindrical reaction space heated to from 200° C. to 600° C.

EP-A-928 785 describes the use of microstructured mixers for the phosgenation of amines in the gas phase. The use of micromixers has the disadvantage that even very small amounts of solids, whose formation cannot be prevented completely in the synthesis of the isocyanates, can lead to blockage of the mixer, which reduces the time for which the phosgenation plant is available.

However, it is in all cases necessary to effectively stop the reaction after an optimal reaction time in order to prevent formation of solids as a result of subsequent reactions of the isocyanate.

DE 10245704 A1 describes the rapid cooling of a reaction mixture comprising at least one isocyanate, phosgene and hydrogen chloride in a quench zone. The quench zone comprises at least 2 nozzle heads which in turn can each comprise at least 2 individual nozzles. In the quench zone, the reaction gas is mixed with the sprayed liquid droplets. As a result of vaporization of the liquid, the temperature of the gas mixture is reduced quickly, so that the loss of desired isocyanate product as a consequence of high temperatures is reduced. Furthermore, the nozzle arrangement decreases premature contact of the hot reaction gas with the walls of the quench zone, so that the formation of deposits on the surfaces is reduced.

A disadvantage of the process described is the quench times of from 0.2 to 3.0 s, which lead to a significant loss of isocyanate which needs to be avoided.

The international patent application WO 2005/123665 describes a process in which a reaction mixture comprising isocyanate, phosgene and hydrogen chloride travels from the reaction zone to the quench zone through a zone having a reduced cross-sectional area. An advantage of the process described is that owing to the velocity increase effected thereby, cooling of the reaction mixture occurs here and secondary atomization of the quenching liquid is achieved as a result of the increased velocity of the reaction mixture leaving the zone having a reduced cross-sectional area, so that a larger phase interface between reaction mixture and quenching liquid is obtained and this in turn gives shorter quench times.

The narrowing of the cross section can have the disadvantage that, especially in the case of small apparatus dimensions, small cross-sectional areas are more susceptible to problems due to the deposition of solid impurities or by-products.

It was an object of the invention to develop a process for preparing isocyanates in the gas phase which is operationally stable and in which the reaction is stopped within sufficiently short times after the optimal residence time and simple separation of the isocyanate from the other constituents of the reaction mixture can be achieved.

This object has been able to be achieved by a process for preparing isocyanates from the corresponding amines and phosgene, in which the reaction is carried out in the gas phase in at least one reaction zone and the reaction mixture is passed through at least one zone in which the reaction mixture is brought into contact with at least one liquid to stop the reaction, wherein a region having a cross section which is widened compared to the reaction zone or constant, preferably widened, is present between the reaction zone and the zone in which the reaction is stopped.

The term reaction space refers to the volume in which at least 98% of the conversion, i.e. the consumption of the amine used, takes place, preferably at least 99%, particularly preferably 99.5%, very particularly preferably 99.7%, in particular 99.9% and especially 99.99%. The volume located downstream of the reaction space then represents the intermediate volume between reaction space and quench.

The zone in which at least one liquid is sprayed in will here be referred to as quench zone, and the spraying-in of the liquid will be referred to as quenching.

The way in which the reaction is carried out and the type of reaction zone do not play any significant role in the process of the invention, as long as the phosgenation takes place in the gas phase.

As reaction zone, it is possible to use, for example, tube reactors, flow tubes with or without internals or plate reactors.

The reaction of the amine with the phosgene in the gas phase in the reaction zone can be carried out under the known conditions.

Mixing of the reaction components amine and phosgene can be effected before or in the reactor. Thus, it is possible for the reactor to be preceded by a mixing unit, for example a nozzle, as a result of which a mixed gas stream comprising phosgene and amine enters the reactor.

In a possible embodiment, the phosgene stream, if appropriate mixed with an inert medium, is firstly distributed very homogeneously over the entire width of the reactor by means of a distributor element. The amine stream is fed in at the beginning of the reactor where a distributor channel having holes or mixing nozzles is installed in the reaction channel, with this distributor channel preferably extending over the entire width of the reactor. The amine, which may, if appropriate, be mixed with an inert medium, is fed through these holes or mixing nozzles into the phosgene stream.

The inert medium is a medium which is gaseous at the reaction temperature and does not react with the starting materials. For example, it is possible to use nitrogen, noble gases such as helium or argon or aromatics such as chlorobenzene, dichlorobenzene or xylene. Preference is given to using nitrogen as inert medium.

The process of the invention is preferably carried out without an inert medium.

The process of the invention can be carried out using primary amines which can preferably be converted into the gas phase without decomposition. Particularly suitable amines are amines, in particular diamines, based on aliphatic or cycloaliphatic hydrocarbons having from 1 to 15 carbon atoms. Examples are 1,6-diaminohexane, 1-amino-3,3,5-trimethyl-5-aminomethylcyclohexane (IPDA), 1,3- or 1,4-(isocyanato-methyl)cyclohexane (BIC) and 4,4'-diaminodicyclohexylmethane and 3 (or 4),8 (or 9)-bis(aminomethyl) tricyclo [$5.2.1.0^{2.6}$]decane isomer mixtures. Preference is given to using 1,6-diaminohexane (HDA).

The process of the invention can also be carried out using aromatic amines which can preferably be converted into the gas phase without decomposition. Examples of preferred aromatic amines are toluenediamine (TDA), preferably 2,4 or 2,6 isomers or mixtures thereof, diaminobenzene, naphthalenediamine (NDA) and 2,4'- or 4,4'-methylene(diphenylamine) (MDA) or isomer mixtures thereof.

In the process of the invention, it is advantageous to use phosgene in an excess over the amino groups. The molar ratio of phosgene to amino groups is usually from 1.1:1 to 20:1, preferably from 1.2:1 to 5:1.

To carry out the process of the invention, it can be advantageous to preheat the streams of the reactants, usually to temperatures of from 100 to 600° C., preferably from 200 to 500° C., prior to mixing. The reaction in the reaction zone usually takes place at a temperature of from 150 to 600° C., preferably from 250 to 500° C. The process of the invention is preferably carried out continuously.

In a preferred embodiment, the dimensions of the reactor and the flow velocities are chosen so that turbulent flow, i.e. flow having a Reynolds number of at least 2300, preferably at least 2700, with the Reynolds number being formed using the hydraulic diameter of the reactor, prevails. The Reynolds number determines the flow regime and thus the residence time distribution in the reaction tube (H. Schlichting: Grenzschichttheorie, Verlag G. Braun, 1982; M. Baerns: Chemische Reaktionstechnik, Georg Thieme Verlag Stuttgart, 1992).

The gaseous reaction mixture preferably travels through the reaction space at a flow velocity of from 10 to 300 meters/second, preferably from 25 to 250 meters/second, particularly preferably from 40 to 230 meters/second, very particularly preferably from 50 to 200 meters/second, in particular from >150 to 190 meters/second and especially from 160 to 180 meters/second.

The mean contact time of the reaction mixture in the reaction zone is generally in the range from 0.001 seconds to <5 seconds, preferably from >0.01 seconds to <3 seconds, particularly preferably from >0.015 seconds to <2 seconds. In the case of the reaction of (cyclo)aliphatic amines, the mean contact time can very particularly preferably be from 0.015 to 1.5 seconds, in particular from 0.015 to 0.5 seconds, especially from 0.020 to 0.1 seconds and often from 0.025 to 0.05 seconds.

For the purposes of the invention, the mean contact time is the period of time from commencement of mixing of the starting materials to termination of the reaction by the quench. In a preferred embodiment, the flow in the reaction zone in the process is characterized by a Bodenstein number of greater than 10, preferably greater than 100 and particularly preferably greater than 500. The Bodenstein number is a measure of the degree of backmixing in the flow apparatus. The backmixing decreases with increasing Bodenstein number (M. Baerns: Chemische Reaktionstechnik, Georg Thieme Verlag Stuttgart, 1992).

The invention accordingly provides a process for preparing isocyanates by reacting amines with phosgene in the gas phase in at least one reaction zone, in which the reaction mixture is passed through at least one zone in which the reaction mixture is brought into contact with at least one liquid to stop the reaction and, between the reaction zone and the quench zone, the reaction mixture is passed through a zone which has a cross section which is widened compared to the reaction zone or constant, preferably widened. Here, the term "widened" means an increase in the cross section in the main flow direction of the reaction mixture.

The widening of the flow cross section is preferably selected so that the reaction gas is retarded with little if any laminar separation, so that no dead zones which are susceptible to formation of deposits can be formed. The choice of the size of the flow cross section or the widening of the flow cross section depends essentially on experience of the susceptibility to blockage of the apparatus dimensions. Thus, processes having small geometric dimensions based on the characteristic size of the particles are preferably configured with a large widening of the cross section while processes having large geometric dimensions are preferably configured with a constant cross section between reaction zone and quench zone.

This can be chosen differently depending on the amine used: in the case of isocyanates which have a strong tendency to form deposits, a widening of the flow cross section is preferred.

On the other hand, in the case of isocyanates which have a low tendency to form deposits, a constant flow cross section will be sufficient.

Isocyanates which have a strong tendency to form deposits are, in particular, monoisocyanates and (cyclo)aliphatic isocyanates, in particular hexamethylene 1,6-diisocyanate.

In contrast, isocyanates which have a low tendency to form deposits are, for example, aromatic isocyanates and in particular tolylene diisocyanate.

As a general rule, the tendency of isocyanates to form deposits increases with increasing functionality, increasing reactivity and/or increasing molecular weight.

The Mach number of the flow in the intermediate zone is, for example, from 0.05 to 0.95, preferably from 0.1 to 0.9 and particularly preferably from 0.2 to 0.85. The Mach number is the ratio of the local flow velocity to the local speed of sound in the reaction mixture. The Mach number requirements directly determine, in the case of the given stream, the size of the cross section in the intermediate volume between reaction space and quench.

The ratio of flow cross section in the widened area to the flow cross section in the reaction zone is from >1:1 to 4:1, preferably from 1.1:1 to 3:1 and particularly preferably from 1.2:1 to 2:1.

The term "flow cross section" here refers to the cross-sectional area, i.e. the area perpendicular to the main flow of the reaction mixture bounded by the interior dimensions of the apparatus. The ratio of the flow cross sections is formed between the smallest possible flow cross section of the reaction zone and the flow cross section at the inlet to the quench.

In the case of the widening of the cross section, the shape and length of the transition region between reaction zone and entry into the quench region is preferably selected so that very little separation of the flow occurs. The way in which the transition has to be configured as a function of the shape of the cross section of the reaction zone and the inlet cross section for no separation to occur is known to those skilled in the art. In the case of, for example, a straight circular reaction tube and circular inlet cross section into the quench zone, separation can be achieved by selection of a transition cone having a cone half-angle of, for example, less than 20°, preferably less than 15°, particularly preferably less than 10°, very particularly preferably less than 7.5° and in particular less than 5°. The cone half-angle is the angle made by the wall in the widening to the longitudinal axis of the reaction tube.

The transitions between the sections can be stepwise or rounded. Preference is given to a rounded design.

The length of the intermediate zone is given trigonometrically by the cone half-angle and the ratios of the flow cross sections.

In the quench zone, the reaction mixture which consists essentially of the isocyanates, phosgene and hydrogen chloride is intensively mixed with the liquid sprayed in. Mixing is carried out so that the temperature of the reaction mixture is reduced from an initial 150 to 600° C., preferably 250 to 500° C., in the reaction zone and then by 50 to 300° C., preferably by 100 to 250° C., in the quench zone and part or all of the isocyanate comprised in the reaction mixture goes over into the sprayed-in liquid droplets as a result of condensation and solubility, while the phosgene and the hydrogen chloride remain essentially completely in the gas phase. The quench preferably reduces the temperature of the reaction mixture to 100 to 200° C., preferably 120 to 180° C., particularly preferably 120 to 150° C., at the end of the quench zone.

The proportion of the isocyanate comprised in the gaseous reaction mixture which goes over into the liquid phase in the quench zone at a temperature of from 120 to 150° C. is preferably from 20 to 100% by weight, particularly preferably from 40 to 100% by weight and in particular from 50 to 100% by weight, based on the isocyanate comprised in the reaction mixture.

The proportion of the hydrogen chloride comprised in the gaseous reaction mixture which goes over into the liquid phase in the quench zone is preferably less than 20% by weight, particularly preferably less than 15% by weight, very particularly preferably less than 10% by weight, in particular less than 5% by weight and especially less than 2% by weight.

The proportion of the phosgene comprised in the gaseous reaction mixture which goes over into the liquid phase in the quench zone is preferably less than 20% by weight, particularly preferably less than 15% by weight, very particularly preferably less than 10% by weight and in particular less than 5% by weight.

The reaction mixture preferably flows through the quench zone from the top downward. Below the quench zone, there is a collection vessel in which the liquid phase is precipitated, collected and removed via an outlet and is subsequently worked up in a manner known per se. The remaining gas phase is removed via a second outlet and is likewise worked up in a manner known per se.

The liquid droplets in the quench are produced by means of single- or two-fluid atomizer nozzles, preferably single-fluid atomizer nozzles, and preferably have a Sauter mean diameter $D_{32}$ of from 5 to 5000 μm, particularly preferably from 5 to 500 μm and in particular from 5 to 250 μm.

The Sauter mean diameter $D_{32}$ (SMD) describes, except for a constant factor, the ratio of the mean droplet volume to the mean droplet surface area (cf. K. Schwister: Taschenbuch der Verfahrenstechnik, Fachbuchverlag Leipzig, Carl Hanser Verlag 2003) and is thus the important parameter of the droplet size distribution produced in the quenching process. It is the droplet diameter at which the volume/surface area ratio is the same as that for the sum of all droplets in the ensemble under consideration and indicates the degree of fineness of the atomization with regard to the particle surface area.

The atomizer nozzles produce, depending on the embodiment, a spray cone angle a of from 10 to 140°, preferably from 10 to 120°, particularly preferably from 10° to 100°.

The number of atomizer nozzles is not restricted and can, for example, depending on the inlet for the reaction mixture, be from 1 to 10, preferably from 1 to 6, particularly preferably from 1 to 4, very particularly preferably from 1 to 3 and in particular from 1 to 2.

The output from one reaction zone is preferably conveyed into the quench zone, but it is also possible for the outputs from a plurality of reaction zones to be fed via one or more inlets into one quench zone.

It is also possible to divide up the output from a reaction zone and feed it via a plurality of inlets into one or more quench zones.

FIG. 1 shows the definition of the spray cone angle α: the spray cone angle α is the angle in the tip of the cone which encloses the volume in which 50 percent by mass of all droplets travel.

According to the invention, a widening of the cross section or a section with constant cross section, depending on the apparatus dimensions, by means of which, in the case of subsonic flow in the reaction zone, a slight compression associated with a concentration change in the constituents of the reaction gas is achieved is present between the reaction zone and the quench zone. Since, compared to an arrangement having a significant narrowing of the cross section between reaction zone and quench zone, only a small degree of secondary atomization of the quenching liquid can be achieved by means of the stream of reaction mixture, care has to be taken to ensure that the droplets fed into the quench zone have a very low Sauter mean diameter and thus a particularly high specific droplet surface area, so that the desired rapid decrease in the temperature of the reaction mixture can be achieved.

The loss of valuable isocyanate product as a result of further reaction to form by-products can be minimized in this way.

The ratio of the free flow cross section in the quench zone to the free flow cross section in the reaction zone is from 25/1 to 1/2, preferably from 10/1 to 1/1.

The liquid which is sprayed in via the atomizer nozzles has to have a good solvent capability for isocyanates. Preference is given to using organic solvents. In particular, use is made of aromatic solvents which can preferably be substituted by halogen atoms. Examples of such liquids are toluene, benzene, nitrobenzene, anisole, chlorobenzene, dichlorobenzene (ortho, para), trichlorobenzene, xylene, hexane, diethyl isophthalate (DEIP) and also tetrahydrofuran (THF), dimethylformamide (DMF) and mixtures thereof.

In a preferred embodiment of the process of the invention, the liquid sprayed in is a mixture of isocyanates, a mixture of isocyanates and solvent or isocyanate, with the quenching liquid used in each case being able to have proportions of low boilers such as hydrogen chloride and phosgene. Preference is given to using the isocyanate which is prepared in the respective process. Since the reaction stops as a result of the decrease in temperature in the quench zone, subsequent and secondary reactions with the isocyanates sprayed in can be substantially ruled out. The advantage of this embodiment is, in particular, that it is not necessary to separate off the solvent.

The temperature of the liquid sprayed in is preferably from 0 to 300° C., particularly preferably from 50 to 250° C. and in particular from 70 to 200° C., so that the desired cooling and condensation of the isocyanate is achieved by the amount of liquid sprayed in.

The liquid sprayed in preferably has a low solvent capability for phosgene and/or hydrogen chloride. The temperature of the liquid sprayed in is particularly preferably sufficiently high for, in particular, the gaseous components phosgene and/or hydrogen chloride to dissolve in the quenching liquid to only a small extent in accordance with Henry's law.

The velocity of the reaction gas in the quench zone is preferably greater than 1 m/s, particularly preferably greater than 10 m/s and in particular greater than 20 m/s.

To achieve rapid cooling of the gaseous reaction mixture in the quench zone and rapid transfer of the isocyanate into the liquid phase, the droplets of the liquid sprayed in have to be finely dispersed over the entire flow cross section of the reaction gas very quickly. The desired temperature decrease and the desired transfer of the isocyanate into the droplets generally takes $10^{-4}$ seconds or more, particularly preferably at least $5 \times 10^{-4}$ seconds and in particular at least 0.001 second. The desired temperature decrease and the desired transfer of the isocyanate into the droplets is preferably carried out in up to 10 seconds, particularly preferably in up to 1 second and in particular in up to 0.2 second.

The times taken for transfer of the isocyanate into the droplets are defined as the period of time between entry of the reaction gas into the quench region and the point in time at which the reaction gas deviates by 10% from the adiabatic final temperature of the mixture of reaction gas and droplets. A loss of isocyanate by means of secondary or further reactions can be avoided virtually completely by means of the chosen periods of time.

The velocity at which the droplets leave the nozzle depends on the type of atomization and is generally at least 15 m/s, preferably at least 40 m/s and particularly preferably at least 100 m/s. The upper limit of the velocity is not critical. A velocity of up to 350 m/s is frequently sufficient.

The mass ratio of the amount of liquid sprayed in to the amount of the gaseous reaction mixture is preferably from 100:1 to 1:10, particularly preferably from 50:1 to 1:5 and in particular from 10:1 to 1:2.

As indicated above, a quench zone is located after the reaction zone. The liquid phase and gas phase taken from the quench zone are worked up. When a solvent is used as atomized liquid, a separation of isocyanate and solvent is carried out, usually by means of distillation which is known per se. The gas phase, which comprises essentially phosgene, hydrogen chloride and possibly isocyanate which has not been separated off, can likewise be separated into its constituents, preferably by distillation or adsorption which are known per se, with the phosgene being able to be recirculated to the reaction and the hydrogen chloride being able to be either utilized for further chemical reactions, processed further to give hydrochloric acid or dissociated into chlorine and hydrogen again.

FIG. 3 shows an embodiment of the process of the invention with a constant cross-sectional area between reactor and quench. FIG. 3a: side view.

Figure 1:
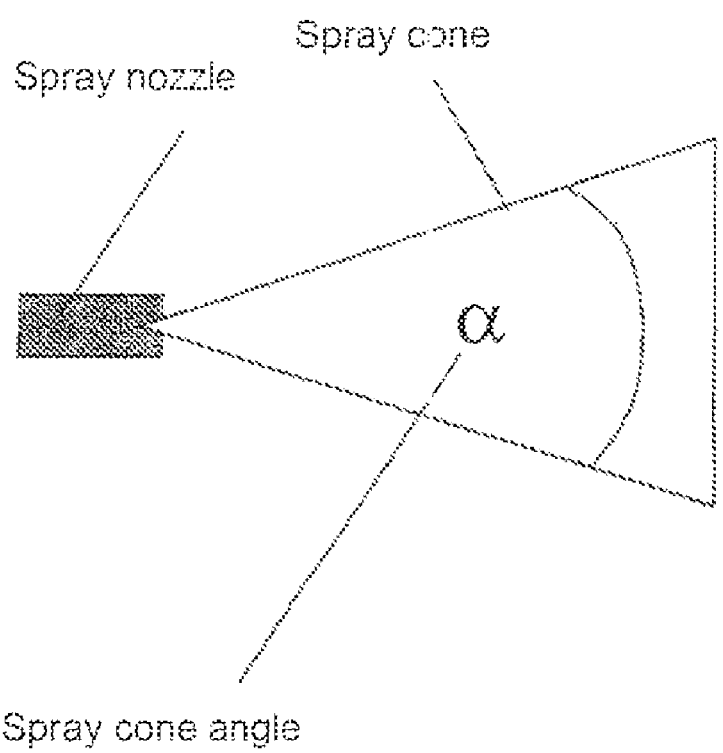
Figure 2:
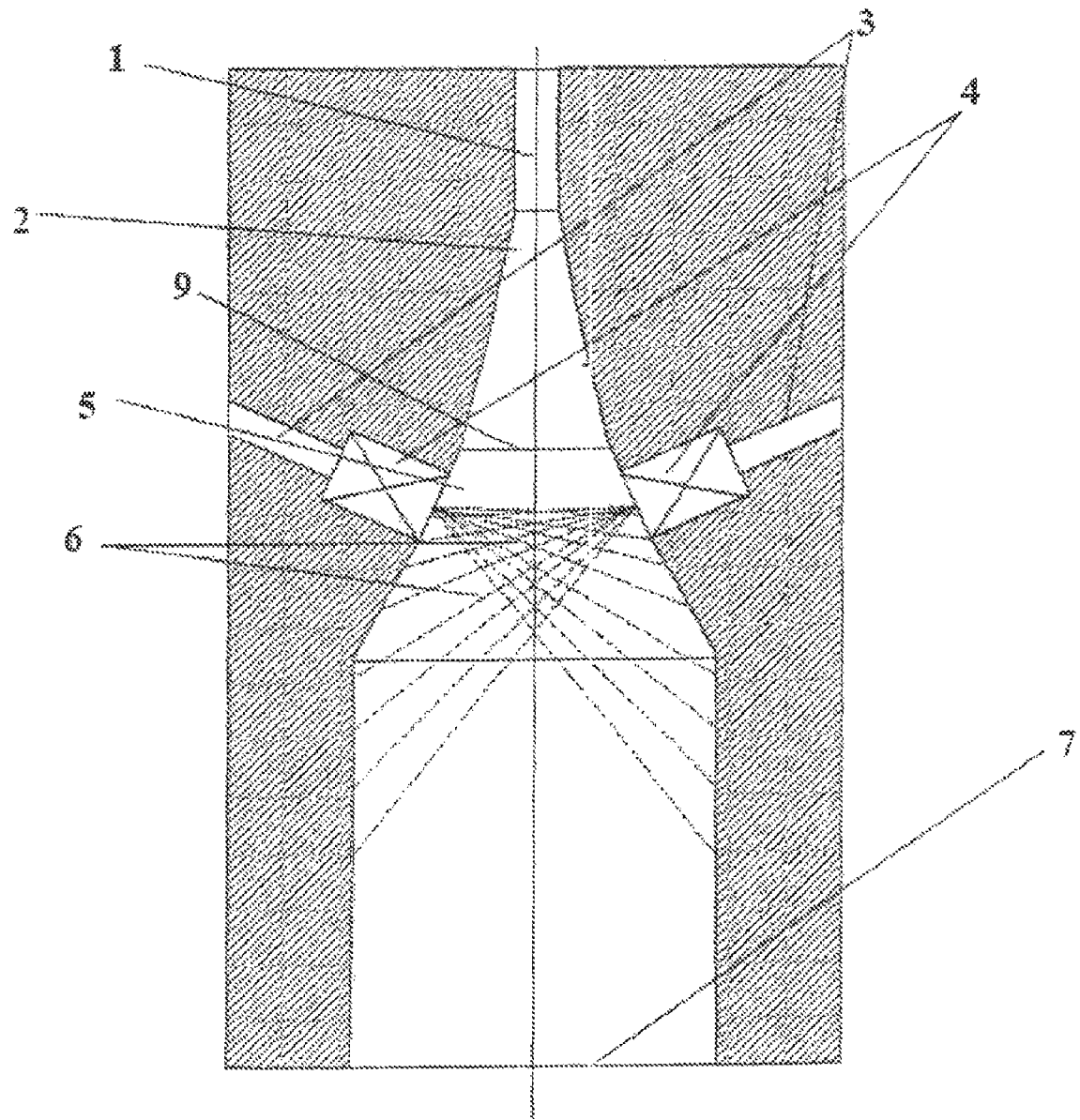
FIG. 2 shows an embodiment of the process of the invention with a widened cross-sectional area between reactor and quench.
Figure 3B:
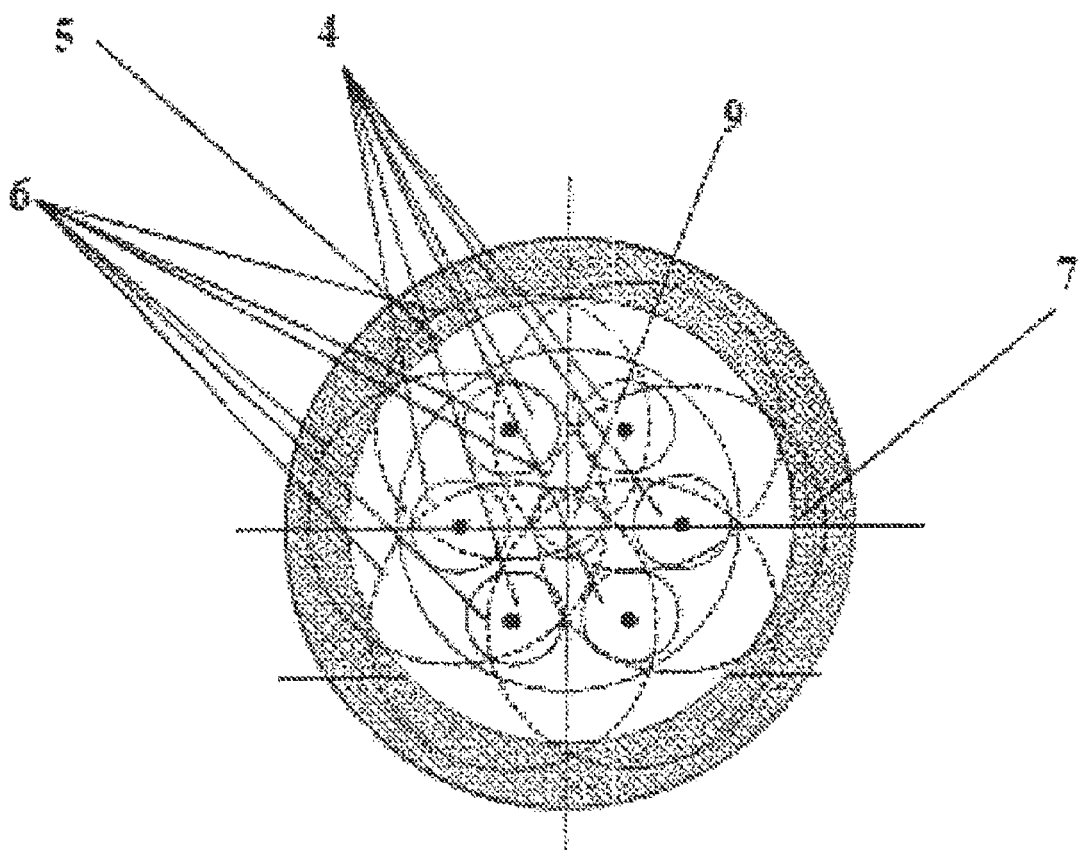
FIG. 3b: section perpendicular to the longitudinal axis, viewed from the direction of the quench zone.

The invention is illustrated by the following examples.

EXAMLE 1

In a tube reactor (diameter 8 mm) and provided with an upstream mixing device, 67.5 kg/h of reaction gas comprising tolylene diisocyanates (2,4 and 2,6 isomer mixture), phosgene and hydrochloric acid were produced.

The reaction gas was then fed via a cross-sectional widening having a diameter of 10 mm into the quench zone. The opening half-angle of the conical widening piece was in this case 5°. In the quench zone there were two individual single-fluid nozzles having a spray cone opening angle of 80°. The nozzles produced droplets having a Sauter mean diameter $D_{32}$ of about 100 μm. The amount of liquid sprayed in was 100 kg/h. The quenching liquid sprayed in was monochlorobenzene. The temperature of the reaction gas on entry into the quench zone was 384° C. and the pressure of the gas was 10.0 bar. The entry temperature of the quenching liquid was 100° C., and the exit velocity of the liquid droplets from the spraying nozzle was about 50 m/s. The residence time of the reaction gas in the quench zone was about 0.015 s. Here, the temperature of the quench gas dropped to about 156° C. The desired temperature decrease thus occurred in less than 0.015 s. The amount of tolylene diisocyanate in the reaction gas mixture decreased by 80% compared to the concentration on entering the quench zone.

List of the Reference Numerals in the Figures:
1 Part of the reaction zone
2 Zone with conical cross-sectional widening
3 Inlet for quenching liquid
4 Atomization device
5 Quench zone
6 Spray cone
7 Liquid and gas outlet
8 Zone having a constant cross section
9 Inlet for reaction mixture

The invention claimed is:
1. A process for preparing isocyanates from the corresponding amines and phosgene, in which the reaction is car- ried out in the gas phase in at least one reaction zone and the reaction mixture is fed into at least one zone into which at least one liquid is sprayed to stop the reaction, wherein a region having a widened cross section is present between the reaction zone and the zone in which the reaction is stopped wherein, in the region of the widening, the wall makes a cone half-angle of less than 20° with the longitudinal axis and wherein a ratio of a free flow cross section in said quench zone to a free flow cross section in said reaction zone is from 10/1 to 25/1.

2. The process according to claim 1, wherein tube reactors, flow tubes with or without internals or plate reactors are used as the reaction zone.

3. The process according to claim 1, wherein the ratio of the flow cross section in the widened region to the flow cross section in the reaction zone is from 1:1 to 4:1.

4. The process according to claim 1, wherein the liquid droplets sprayed in have a Sauter mean diameter of from 5 to 5000 μm.

5. The process according to claim 1, wherein the temperature of the reaction mixture is from 150 to 600° C.

6. The process according to claim 1, wherein the liquid sprayed in is an organic solvent.

7. The process according to claim 1, wherein the liquid sprayed in is an aromatic solvent which may be substituted by halogen atoms.

8. The process according to claim 1, wherein the liquid sprayed in is an isocyanate.

9. The process according to claim 1, wherein a transition between said reaction zone and said zone in which said reaction is stopped is a rounded design.

10. The process according to claim 1, wherein a gaseous reaction mixture travels through said reaction zone at a flow velocity of from 10 to 300 m/s.

11. The process according to claim 1, wherein a gaseous reaction mixture travels through said reaction zone at a flow velocity of from 160 to 180 m/s.

12. The process according to claim 1, wherein a mean contact time of said reaction mixture in said reaction zone is from 0.001 to <5 seconds.

13. The process according to claim 1, wherein said at least one liquid is selected from the group consisting of toluene, benzene, nitrobenzene, xylene, hexane, diethyl isophthalate, tetrahydrofuran, dimethylformamide and a mixture thereof.

14. The process according to claim 1, wherein a reaction gas has a velocity in said quench zone of greater than 1 m/s.

15. The process according to claim 1, wherein a mass ratio of an amount of liquid sprayed into and an amount of a gaseous reaction mixture is from 10:1 to 1:2.

16. The process according to claim 1, wherein in the region of the widening, the wall makes a cone half-angle of less than 7.5° with the longitudinal axis.

17. The process according to claim 1, wherein in the region of the widening, the wall makes a cone half-angle of less than 5° with the longitudinal axis.

* * * * *